United States Patent
ten Cate

(10) Patent No.: US 6,352,683 B1
(45) Date of Patent: *Mar. 5, 2002

(54) APPARATUS AND METHOD FOR THE LOCAL DELIVERY OF DRUGS

(75) Inventor: Folkert Jan ten Cate, Rotterdam (NL)

(73) Assignee: Point Biomedical Corporation, San Carlos, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/893,206

(22) Filed: Jul. 15, 1997

Related U.S. Application Data

(63) Continuation-in-part of application No. PCT/NL95/00028, filed on Jan. 19, 1995.

(51) Int. Cl.[7] .............................................. A61B 5/055
(52) U.S. Cl. .................... 424/9.34; 424/9.32; 424/9.51; 424/9.3; 424/9.52; 424/450; 600/453; 600/467; 600/470
(58) Field of Search ................................. 600/470, 467; 600/453; 424/450, 9.3, 9.32, 9.51, 9.52

(56) References Cited

U.S. PATENT DOCUMENTS

| | | | | |
|---|---|---|---|---|
| 5,190,766 A | * | 3/1993 | Isihara ........................ | 424/489 |
| 5,236,410 A | * | 8/1993 | Granou et al. ................ | 600/12 |
| 5,305,757 A | | 4/1994 | Unger et al. ............ | 128/662.02 |
| 5,409,006 A | * | 4/1995 | Buchholtz et al. ..... | 128/660.03 |
| 5,558,092 A | * | 9/1996 | Unger et al. ........... | 128/660.03 |
| 5,580,575 A | * | 12/1996 | Unger et al. ................ | 424/450 |

FOREIGN PATENT DOCUMENTS

| | | | |
|---|---|---|---|
| DE | 2758040 | * | 6/1979 |

OTHER PUBLICATIONS

Fernandez–Ortiz et al., "A New Approach for Local Intravascular Drug Delivery", *Circulation*, vol. 89, No. 4, pp. 1518–1522.

Wolinsky, et al., "Use of a Perforated Balloon Catheter to Deliver Concentrated Heparin Into the Wall of the Normal Canine Artery", *JACC*, vol. 15, No. 2, Feb. 1990, pp. 475–481.

English translation for PCT document 95/07072 (corresponding to PCT Application No. PCT/EP94/02806).

* cited by examiner

*Primary Examiner*—Thurman K. Page
*Assistant Examiner*—Robert M. Joynes
(74) *Attorney, Agent, or Firm*—Marshall, Gerstein, & Borun

(57) ABSTRACT

A local and site-specific drug delivery apparatus for delivering a drug to a specific site is characterized by the combination of a carrier material which reflects or absorbs or emits electromagnetic or mechanical (e.g. ultrasonic) vibrations enabling the monitoring of the material, a drug associated with the carrier material, and a local-delivery mechanism for delivering the carrier material and the drug to a specific site. The local-delivery mechanism may comprise a local-delivery catheter, such as a balloon-type catheter, and the drug delivery apparatus may additionally include a monitor for monitoring the delivery of the drug to the specific site, such as an ultrasonic imaging system. The drug delivery apparatus may also include a vibration generator for inducing release of the drug from the carrier material when the carrier material is at the specific site, such as a generator of ultrasonic energy. Alternatively, the local-delivery mechanism may comprise a targeting agent associated with the carrier material, the targeting agent capable of binding to the specific site within the individual. The targeting agent may be a protein or an antibody, such as a glycogen IIa/IIB receptor antibody, Von Willebrand's factor antibody, an antitumor antibody, hepatic cellular antibody, a white blood cell antibody, or antifibrin.

15 Claims, 2 Drawing Sheets

APPARATUS AND METHOD FOR THE LOCAL DELIVERY OF DRUGS

This is a continuation-in-part of International application PCT/NL95/00028 filed Jan. 19, 1995.

BACKGROUND OF THE INVENTION

The present invention relates to an apparatus and method for the local delivery of drugs.

Local delivery of drugs has been previously accomplished by conjugating a drug to biocompatible or biodegradable macromolecules, e.g. biopolymers, lipids, polysaccharides, proteins including albumin and immunoglobulines, which have a particular receptor specificity. In this way the drug can be transferred to a particular part of the human body which is subject to treatment with the particular drug. For example, Oppenheim. et al. disclose in U.S. Pat. No. 4,107,288 a process for the preparation of drug containing gelatine particles having a diameter mainly below 500 $\mu$m which can be administered parenterally.

Solid serum albumin spherules having 5 to 30% by weight of an entrapped drug are disclosed by Yapel, Jr. in U.S. Pat. No. 4,147,767. The spherules are particularly suited for intravenous injection into the human body whereafter the drug is released from the spherule in a biphasic manner having an initial fast-release phase followed by a slow release phase.

A method of preparing aqueous suspensions of drug containing spherules comprising a phospholipid has been described by Suzuki, et al. in U.S. Pat. No. 4,016,100. These spherules, which are suitable for injection as well as oral administration, give controlled release of the entrapped drug after administration.

Although the particles and spherules described above can be used to deliver a drug to a particular part of the body, e.g. the lungs or the liver, a local and site specific actively controlled release of the drug contained by said particles and spherules has not be achieved in the prior art. Actively controlled release refers to the ability to spatially localize, modulate, and monitor the delivery of drugs for optimal benefit. In a mammal, i.e. a human or animal, the release of the drug contained by said particles and spherules is determined by the biological processes and functions of the mammalian body, i.e. the biodegradation of the particles, and can not be influenced actively and/or in a site specific manner.

It is therefore not unlikely that while being transferred to the desired area in the mammalian body by the blood circulation, these drug containing particles and spherules described in the prior art may be partly inactivated or even disintegrated. Obviously this will give rise to serious consequences for the patient, especially when drugs are used which are highly toxic to the mammalian body. Consequently, the efficacy of the methods described above for treating a certain disorder can be considered to be rather low.

In addition, the prior art does not provide a method for monitoring the release of a drug from particles and spherules neither in space nor in time. Hence, the effective concentration of the drug in the desired area of the mammalian body can therefore not be determined.

The present invention relates to particles and spherules which interact with energy in-situ to modulate the release of drugs and also allow detection of the particles and spherules from the energy interactions. Biocompatible or biodegradable macromolecules labelled with solid gold particles, e.g. gold-albumin, have found application as cytochemical markers in electron microscopy. Solid gold particles bind the macromolecule irreversibly whereby the macromolecule generally preserves its specific biological activity. Because of their high electron density, these gold particles can be observed by electron microscopy enabling the detection of intercellular locations of the macromolecule. Such systems have been described by Horisberger, et al., Histochem. 80, 1984, 13–18, and by Slot, et al., Eur. J. Cell Biol. 38, 1985, 87–93. However, neither Horisberger, et al. nor Slot, et al. describe or suggest that these gold-albumin particles can be used as local drug delivery systems.

Particles prepared from biocompatible or biodegradable materials, which can be detected by ultrasonic imaging are known as well. These particles comprise so-called microparticles, microbubbles, microspheres or microcapsules containing gaseous components capable of reflecting ultrasonic waves. WO-9.112.823 discloses a process for preparing such particles comprising the formation of water-dispersable, preferably proteinaceous, microcapsules having a liquid or solid core by conjugation of oil/water bubbles with biocompatible or biodegradable materials, e.g. albumin, followed by the removal of at least some of said liquid or solid to create a microcapsule containing a gas. The microcapsules are preferably 0.1 to 500 $\mu$m in diameter. In WO-9.112.823 it is neither described nor suggested that such particles can be used for the active and controlled delivery of a drug to a specific area of the mammalian body.

The problems which are encountered when the above described systems are used for the local delivery of a drug can be summarized as follows: 1) the release of the entrapped drug from the local drug delivery system can not be controlled actively and/or in a site specific manner, 2) before the systems reach the area in the mammalian body to be treated they might be inactivated or even disintegrated, and 3) the release and/or the effective concentration of the drug in the area to be treated can not be determined.

SUMMARY OF THE INVENTION

The present invention is directed to a local and site-specific drug delivery system for delivering a drug to a specific site. The drug delivery system is characterized by the combination of a carrier material which reflects or absorbs or emits electromagnetic or mechanical (e.g. ultrasonic) vibrations enabling the monitoring of the material, a drug associated with the carrier material, and local-delivery means for delivering the carrier material and the drug to a specific site.

The local-delivery means may comprise a local-delivery catheter, such as a balloon-type catheter, and the drug delivery system may additionally include means for monitoring the delivery of the drug to the specific site, such as an ultrasonic imaging system. The drug delivery system may also include means for inducing release of the drug from the carrier material when the carrier material is at the specific site, such as means for generating electromagnetic or mechanical vibrations.

The carrier material may comprise an ultrasonic contrast agent in the form of microparticles, microbubbles, microspheres or microcapsules. The carrier material may comprise microbubbles having a diameter of between 1–1000 $\mu$m, between 1–100 $\mu$m, or between 1–20 $\mu$m.

Alternatively, the local-delivery means may comprise a targeting agent associated with the carrier material, the targeting agent capable of binding to the specific site within the individual. The targeting agent may be a protein or an antibody, such as a glycoprotein IIa/IIB receptor antibody, Von Willebrand's factor antibody, an antitumor antibody, hepatic cellular antibody, a white blood cell antibody, or antifibrin antibody.

The carrier material may be in the form of an ultrasonic contrast agent, such as gas microbubbles having a gas and a shell, wherein the drug is embedded in the microbubble shell, encapsulated in the microbubble, or bound to a surface of the microbubble shell. The targeting agent may be bound to a surface of the microbubble shell.

The drug, which may comprise a chemotherapy agent, a thrombolytic drug, an anti-infection agent, vasodilation agent, tissue protective agent, or a gene therapy agent, may be selected from the group consisting of acebutolol, acetylsalicylic acid, adenosine, ATP, alfentanil, alprazolam, azlocillin, betamethasone, bleomycin, captopril, carbenicillin, cefamandole, cefazolin, cefonicid, ceforanide, cefotaxime, cefoxitin, clonidine, cloxacillin, cyclophosphamide, cytarabine, dexamethasone, dicloxacillin, diazepam, diazoxide, digitoxin, digoxin, diltiazem, diphenhydramine, disopyramide, doxorubicin, doxycycline, ceftazidime, ceftizoxime, cefuroxime, cephalexin, cephalothin, cephapirin, chloramphenicol, chloroquine, chlorothiazide, chlorpropormide, chlorthalidone, cimetidine, clofibrate, ibuprofen, imipramine, indomethacin, isosorbide dinitrate, ketoprofen, labetalol, lidocaine, lorazepam, lorcainide, meperidine, mercaptopurine, methadone, methicillin, erythromycin, ethambutol, fentanyl, flucytosine, flunitrazepam, fluorouracil, flurazepam, furosemide, gold sodium thiomalate, haloperidol, heparin, hexobarbital, hydrochlorothiazide, nortriptyline, oxacillin, oxazepam, phenobarbital, phenylbutazone, phenytoin, pindolol, prazosin, prednisolone, prednisone, protenecid, procainamide, propranolol, methothexate, methyldopa, methylprednisolone, metoprolol, metronidazole, mexiletine, mezlocillin, minocycline, morphine, moxalactam, nadolol, nafcillin, naproxen, nifedipine, nitrazepam, theopental, ticarcillin, timolol, tocainide, tolbutamide, tolmetin, triamterene, triazolam, trimethoprim, tubocurarine, urokinase, valproic acid, verapamil, warfarin, protriptyline, pyrimethamine, quinidine, ranitidine, rifampin, salicylic acid, streptomycin, streptokinase, sulfadiazine, sulfamethoxazole, sulfisoxazole, ternazepam, terbutaline, tetracycline, theophylline, andtissue plasminogen activator (tpa).

The invention is also directed to a method of treating a specific site in a mammal with a drug. The method is characterized by the steps of: (a) providing a carrier material which reflects or absorbs or emits electromagnetic or mechanical vibrations enabling the monitoring of the material and a drug associated with the carrier material, and (b) delivering the carrier material and the drug to a specific site in a mammal.

The method may also include the step of generating an image of the carrier material at the specific site, such as by ultrasonically generating an image of the carrier material at the specific site, and/or the step of inducing the drug to be released from the carrier material when the carrier material and the drug are at the specific site. The method may further include the step of inducing the drug to be released from the carrier material when the carrier material and the drug are at the specific site by subjecting the carrier material to ultrasonic vibrations.

The invention is also directed to a method of delivering a drug to a specific target site in an individual having the steps of (a) administering an ultrasonic contrast agent-drug complex to an individual, wherein the complex comprises an ultrasonic contrast agent, a drug, and optionally, a targeting agent capable of binding the ultrasonic contrast agent to the target site in the individual, (b) monitoring the individual using ultrasound to determine an arrival of the complex at the target site in the individual, (c) releasing the drug at the target site by applying sufficient energy to rupture the complex at the target site, and (d) optionally, imaging the target site using ultrasound techniques to monitor release of the drug. The target site in a patient for many applications may be generalized areas of tissue or an organ of known anatomical location such as the heart or kidneys. The general area could be irradiated with sufficient energy for drug release without imaging the target site.

These and other features of the present invention will be apparent to those of ordinary skill in the art in view of the detailed description of the preferred embodiment, which is made with reference to the drawings, a brief description of which is provided below.

DETAILED DESCRIPTION OF THE PREFERRED EMBODIMENTS

Figure 1:
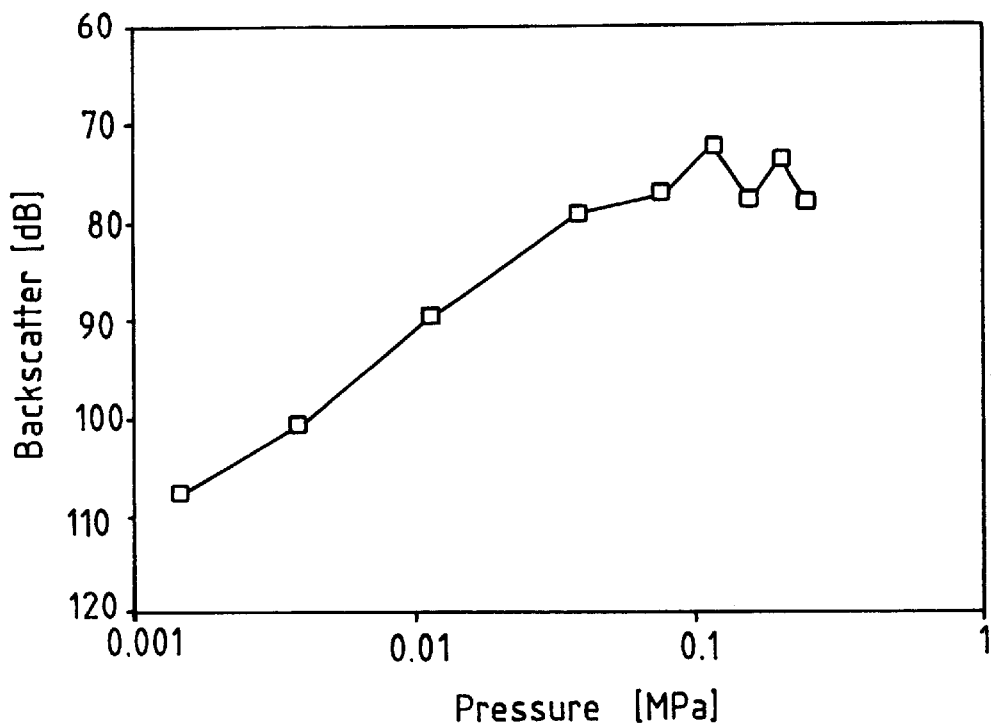
FIG. 1 illustrates the relation between acoustic pulse pressure and reflected backscatter when a 2.5 MHz transducer was used in connection with one example in accordance with an example described below.

The present invention offers a solution for the problems noted above by providing a local drug delivery system containing a drug as well as a method for the active and site specific alteration of the release properties of the local drug delivery system, once the delivery system has been administered to the mammalian body. According to the invention, this is carried out by means of electromagnetic and/or mechanical vibrations. The invention further provides such a method which enables the monitoring of the release.

The present invention therefore relates to a local drug delivery system comprising: a) a local and site specific drug delivery system, comprising b) a material which reflects or absorbs or emits electromagnetic and/or mechanical vibrations enabling the active control of drug release and/or the monitoring of the material, e.g. by imaging techniques, and c) a drug.

A local and site specific drug delivery system is intended to be a system, comprising biocompatible or biodegradable materials, which is capable of transferring or carrying a drug to a specific area or site, e.g. an organ or organella, at which specific area or site the system releases the drug in an active and controlled manner enabling the interaction of the drug with the specific area or site, when—prior to or after administration of the drug delivery system to the human or animal body—the site is treated with electromagnetic and/or mechanical vibrations.

In this application electromagnetic and/or mechanical vibrations are intended to comprise vibrations or waves, which are reflected or absorbed or emitted, and propagated in the form of energy through a space or through a material medium. Examples of such vibrations or waves are cosmic rays, gamma rays, X-rays, ultraviolet-, visible and infrared waves, sound waves, microwaves and radiowaves, streams of sub-atomic particles, e.g. alpha-rays, beta-rays and photons, and the like.

Preferably, the vibrations are not harmful to the mammalian body as will be clear to one skilled in the art, although it is possible to use vibrations (or radiation) which also have therapeutic value, e.g. in cytostatic treatment.

The expression "imaging techniques" is intended to encompass techniques by which the electromagnetic and/or mechanical vibrations can be detected or monitored, and such techniques will described hereinbelow and/or will be clear to one skilled in the art. In principle, any usual imaging technique for use in medical procedures can be used to follow the drug, its concentration at specific sites of the body, and/or the release of the drug therefrom.

Although the invention is not limited to this mechanism, preferably the interaction of the vibrations with the drug delivery system will lead to or trigger the degradation of the delivery system at the specific site treated with the vibrations, or make the delivery system more susceptible to biological degradation, thereby providing for the local and site specific release of the drug. The degradation and thereby said release can then be followed by means of the above-mentioned imaging techniques.

It will furthermore be clear to one skilled in the art that the site of the release of the drug can be controlled by controlling the vibrations, i.e. by only treating those sites at which release of the drug is desired. Furthermore, in most cases— and preferably—the rate of degradation and thereby the rate of release is controlled by the amount of vibrations used, i.e. by controlling the intensity or the time of the treatment.

The local and site specific delivery system will therefore comprise a material that can interact with electromagnetic and/or mechanical vibrations, causing alteration of the release properties of said system. Said interaction preferably leads to an enhancement of the release properties, so that by means of the vibrations the release of the drug contained in said system can be effected in a local and site specific manner. For instance, the interaction of the vibrations can lead to or trigger the partial destruction of the walls of the delivery system, or make it more susceptible to biological degradation as described hereinabove.

Although the preparation of the invention will usually comprise b) a material which reflects or absorbs or emits electromagnetic and/or mechanical vibrations enabling the monitoring of said material by imaging techniques, it will be clear to one skilled in the art that component b) can be omitted when component a) -i.e. the local and site specific drug delivery system—itself is made of a material that reflects or absorbs or emits electromagnetic and/or mechanical vibrations, enabling the monitoring of said system by imaging techniques.

Additionally, according to the invention, the release of the drug can be monitored without simultaneously altering the release properties of the drug delivery system, for instance when two types of vibrations are used, e.g. a first type for altering the release properties and a second type for the subsequent monitoring of the release of the drug. It is also possible to follow the biological release from the delivery system.

Furthermore, it is possible to alter the release properties and monitor the release of the drug at the same time, using the same or different vibrations for achieving these two objectives.

According to the invention, the preparation described above may be administered by a catheter-based intravascular delivery system. Local intravascular administration by means of a catheter is a common technique in medical practice. For example, catheters as double balloon, porous balloon, microporous balloon, stent in a balloon, hydrogel, dispatch and iontophoresis may be used.

For intravenous injection in mammals the preparation according the invention must be smaller than 10 $\mu$m because otherwise they can not pass the capillary circulation of various organ systems. For direct intra arterial injections, however, the preparation may be larger, although it is preferred that their size does not exceed 50 $\mu$m. Consequently, to ensure safe parenteral administration the size of the preparation according the invention is determined by their intended use (parenteral intravenous or parenteral intra arterial).

Preferably, the present invention provides a preparation that comprises as constituent of component a) and/or as component b) a material that can be monitored by ultrasonic imaging and/or an ultrasonic contrast agent, respectively.

In the description of this application an ultrasonic contrast agent comprises a material, which is a chemical substance or compound, either in the gaseous, liquid or solid state, or a particle comprising biocompatible or biodegradable materials such as polysaccharides, proteins, including albumin, and immunoglobulines and which may be in the form of a microparticle, microbubble, microsphere or microcapsule, or a particle comprising synthetic or natural polymers, and the like, and which is capable of reflecting vibrations, preferably ultrasonic vibrations. This description of an ultrasonic contrast agent is, however, not intended to be limited to ultrasonic vibrations reflecting materials only, but also to include materials capable of reflecting or absorbing or emitting other electromagnetic and/or mechanical vibrations. The preparation of the present invention preferably reflects ultrasonic waves, which can be monitored by ultrasonic imaging.

Preferably, the preparation of the present invention comprises a material, wherein said material which reflects or absorbs or emits electromagnetic and/or mechanical vibrations, preferably ultrasonic vibrations, can be monitored by clinical ultrasound imaging, including Doppler flow, color Doppler and color tissue imaging methods as well as ultrasound imaging based on techniques using the high frequency imaging (Rf signal) by reflected backscatter, color imaging, Doppler imaging or phenomena based on frequency shifts and second harmonic imaging.

The preparation of the present invention can be used for inducing and monitoring local and site specific drug delivery for use in medical procedures. The preparation releases a drug upon irradiation of said preparation with electromagnetic and/or mechanical vibrations and can be imaged ultrasonically. The preparation is in particular irradiated with ultrasonic waves in a predetermined area and can be imaged ultrasonically in an area including said predetermined area. Consequently, the drug can be imaged ultrasonically in an area including said predetermined area enabling the determination of the rate of the release of said drug as function of space and time.

Preferably, the preparation of the present invention comprises biodegradable particles containing a drug. The particles, when exposed to harmless ultrasonic vibrations at sufficient intensity or during a sufficient period, change their release properties, such as by degradation, thereby releasing the drug. Concurrently, the particles as well as said release can be monitored by means of ultrasonic imaging techniques, using the same harmless ultrasonic vibrations—reflected or absorbed/emitted—that are used for changing the release properties. Because of these advantageous properties, which were not known from the prior art, biodegradable particles are preferred. Suitable biodegradable particles will be clear to one skilled in the art on the basis of the present description, and are for instance described in the prior art mentioned hereinabove.

According to another preferred embodiment, the preparation comprises solid gold containing particles, such as the solid gold albumin particles described hereinabove, and at least one drug. According to this embodiment, the gold-component will serve as component b), as will be clear to one skilled in the art.

The size of the biodegradable and/or gold containing biodegradable particles will be 1–1000 $\mu$m, preferably 1–100 $\mu$m and more preferably 1–20 $\mu$m. Depending on their use, i.e. intravenous or intra arterial, the particles will most preferably have a diameter no larger than 10 $\mu$m or 50 $\mu$m, respectively.

The preparation of the present invention may also comprise preparations in the form or microparticles, microbubbles, microspheres or microcapsules and at least one drug. The size of these microparticles, microbubbles, microspheres or microcapsules will preferably be 1–50 $\mu$m. Depending on their use, i.e. intravenous or intra arterial, the particles will most preferably have a diameter no larger than 10 $\mu$m or 50 $\mu$m, respectively.

These microparticles, microbubbles, microspheres or microcapsules will usually comprise as component b) a material preferably selected from the group comprising gases, aqueous solutions of a contrasting agent and optionally a drug, biocompatible and biodegradable materials.

Although in principle any drug compatible with the components a) and b) can be used as component c), the drug comprised by the above mentioned preparation is preferably elected from the group comprising oncological agents, viral vectors, growth factors, antibiotics, antihypertensive drugs, vasodilators, tissue protective agents, calcium-instream inhibitors, antithrombosis agents and corticosteroids. The preparation may also be used to administer drugs, e.g. antineoplastic drugs, which are highly toxic to health as well as malignant tissue.

Although not limited thereto, the drug will be usually contained inside the preparation or bound thereto, such as by encapsulation or reversible chemical bonds, as will be known to one skilled in the art.

The invention also provides a method for treating specific sites in a mammal comprising the steps of: 1) injecting a drug delivery system into a mammal to thereby alter the acoustic properties of a predetermined area; 2) optionally inducing the release of a drug from said drug delivery system by irradiating said system with electromagnetic and/or mechanical vibrations; and 3) imaging ultrasonically an area including said predetermined area so that an image of said predetermined area is obtained and, when a drug is released, the rate of said release can be determined as function of space and time by said ultrasonic imaging.

By using the preparation of the present invention according to the method described above, drugs can be administered to greater therapeutic advantage. These drugs may be selected from the group comprising oncological agents, viral vectors, growth factors, antibiotics, antihypertensive drugs, vasodilators, tissue protective agents, calcium-instream inhibitors, anti-thrombosis agents and corticosteroids, although any drug known in the art may be selected. The preparation may also be used to administer drugs, e.g. antineoplastic drugs for the treatment of tumors, which are highly toxic to health as well as malignant tissue.

The present invention also provides a method for monitoring the local release of a drug comprising changing of the release properties from an already injected drug delivery system as described hereinabove by irradiating said system with electromagnetic and/or mechanical vibrations, and then imaging ultrasonically the area where the drug is released as function of space and time.

Additionally, the present invention provides a method for altering the release properties of an administered local and site specific drug delivery system of the invention, in which said delivery system is treated with electromagnetic and/or mechanical vibrations, as described hereinabove. Preferably, the release properties are enhanced. Thus, the local and site specific drug delivery system containing a drug is administered to a mammal, such as by injection or another suitable method, whereafter it is transferred to the area to be treated. As soon as the local and site specific drug delivery system has arrived at the area to be treated with the vibrations, its release properties are altered through local and site specific irradiation with said electromagnetic and/or mechanical vibrations, as described hereinabove.

According to a further embodiment, this method further comprises the monitoring of the release of the drug as described herein.

The present invention also provides a method for monitoring the delivery of a drug contained by a local and site specific drug delivery system of the invention in an area in a mammal which is subject to treatment with said drug, by using a suitable monitoring technique, e.g. NMR tomography, X-ray imaging, preferably ultrasonic imaging, enabling the determination of the effective concentration of said drug in space and time in the area which is subject to treatment with said drug.

Preferably, the electromagnetic and/or mechanical vibrations used for altering the release properties of a local and site specific drug delivery system of the invention are also used for the monitoring of the delivery of a drug contained by said local and site specific drug delivery system in an area in a mammal which is subject to treatment with said drug.

The present invention finally provides a method for monitoring the delivery of a drug contained by a local and site specific drug delivery system of the invention by forming an image of the area, which is subject to treatment with said drug and wherein the administered local and site specific drug delivery system is already present, by using a suitable imaging technique, preferably ultrasonic imaging.

The following examples will further illustrate the present invention. It is, however, to be understood that these examples do not restrict the scope of the invention.

EXAMPLE 1

Commercially available albumin microspheres having a diameter in the range of 5 to 30 $\mu$m were administered parenterally by direct intra arterial injection. In this particular example injections were conducted into the left atrium of a pig's heart. Continuous ultrasonic imaging of the heart was performed during the experiment using a commercially available ultrasonic machine (Hewlett Packard Sonos 1000).

The images were recorded on videotape. After 3 to 5 beats after injection an increased video intensity was observed in the left ventricle and thereafter in the muscle of the heart which indicated the pressure of the albumin microspheres in this myocardium. This was also confirmed by an increased video intensity. After one to two hours the video intensity gradually decreased indicating the biodegradation of the albumin microspheres.

In FIG. 1 the relation between acoustic pulse pressure and reflected backscatter is displayed when a 2.5 MHz transducer was used. Below 0.05 MPa (1 Mpa=$10^6$ Pa≈10 atm.) the backscatter intensity was linearly related to the acoustic pressure. Above 0.05 Mpa, however, the backscatter remained constant at higher acoustic pressures showing that the albumin microspheres were destroyed.

EXAMPLE 2

The experiment of Example 1 was repeated with a 3.75 MHz transducer from Hewlett Packard Sonos 1000 and a 5 Mhz transducer from Vingmed. Identical results were obtained, i.e. the microspheres were destroyed at the same pressures.

EXAMPLE 3

Figure 2A:
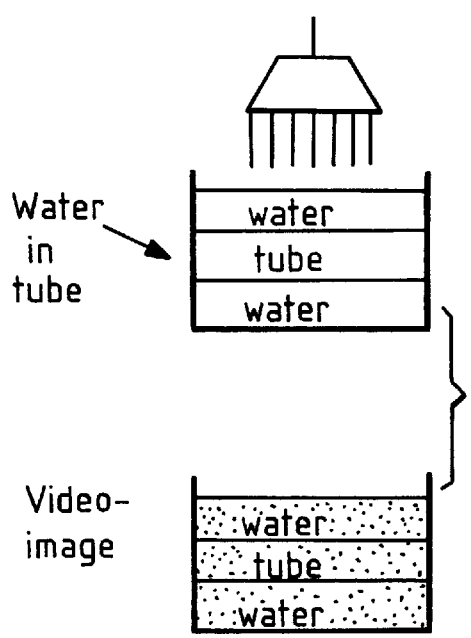
FIG. 2A illustrates the unobservability of a contrast difference when no contrast agent was used in an example described below.

A closed tube containing water was placed in a water containing reservoir. A 2.5, 3.75 or a 5 Mhz transducer was placed in the container and acoustic pressure was applied. An image was visualized by using a television set and the image was subsequently videotaped. Reflections of both edges of the tube were visible which clearly showed the presence of the tube. Because both the container and the tube contained the same fluid, no contrast difference was observed, as shown in FIG. 2A.

Figure 2B:
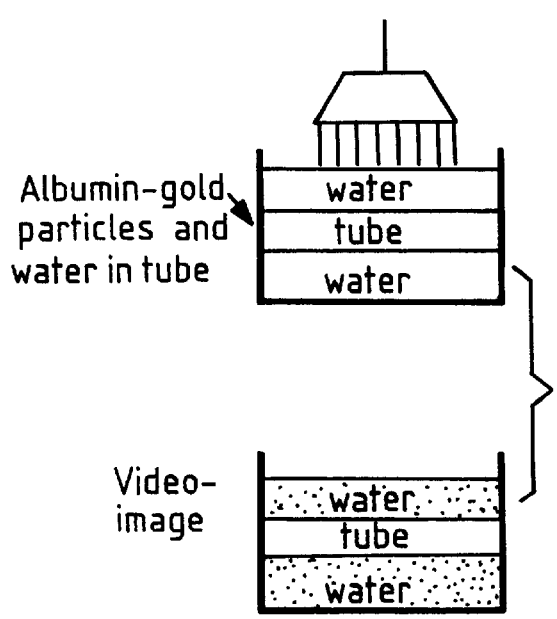
FIG. 2B illustrates the observability of a contrast difference when a contrast agent was used in an example described below.

Next, the tube was filled with water containing commercially available albumin gold particles having a diameter in the range of 10 to 20 μm and placed in the container. On applying acoustic pressure, the image showed a contrast difference between the water contained by the reservoir and that contained by the tube, as shown in FIG. 2B.

First Embodiment

Figure 3:
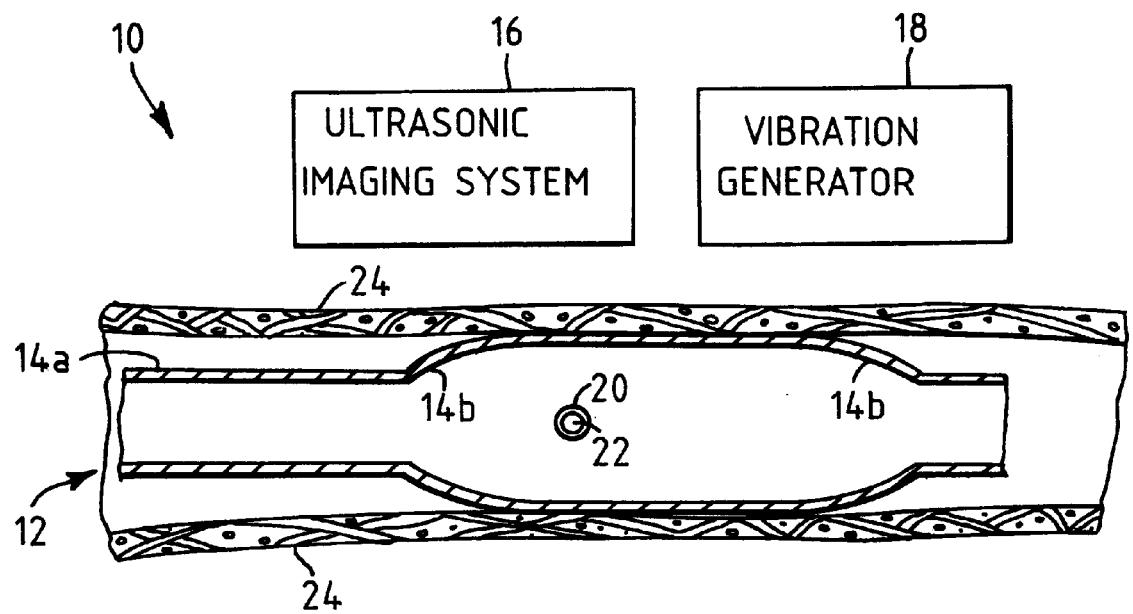
FIG. 3 schematically illustrates a first embodiment of a local drug delivery system in accordance with the invention.

FIG. 3 schematically illustrates a first embodiment of a local drug delivery system 10 in accordance with one aspect of the invention. Referring to FIG. 3, the drug delivery system 10 includes an intravascular catheter (shown in cross-section) in the form of a balloon-type catheter 12 having an elongate flexible tube portion 14a and an expandable balloon portion 14b, an ultrasonic imaging system 16, a vibration generator 18, a carrier material 20 (shown greatly enlarged in the form of a microbubble contrast agent) disposed within the interior of the catheter 12, and a drug 22 associated with the carrier material 20 (shown disposed within the center of the microbubble 20). The catheter 12 is shown disposed within a blood vessel 24, such as an artery or vein.

To use the local drug delivery system 10, the catheter 12, having the carrier material 20 and the drug 22 disposed therein, is inserted into the blood vessel 24 in a conventional manner, and then the fluid pressure within the balloon portion 14b is increased a sufficient amount so that the balloon portion 14b is forced against the interior wall of the blood vessel 24 and so that the carrier material 20 with the drug 22 is forced out of the balloon portion 14b through small holes (not shown) in the balloon portion 14b. Consequently, due to the use of relatively high pressure, the carrier material 20 and the drug 22 will become embedded in the wall of the vessel 24 at the specific site or location of the balloon portion 14b of the catheter 12.

The presence of the carrier material 20 (and the drug 22 within the carrier material 20) at that specific site can be verified by using the ultrasonic imaging system 16. When desired, the drug 22 can be administered to that specific site (by inducing release of the drug 22 from the carrier material 20) with the vibration generator 18 that generates vibrations of sufficient magnitude to collapse the microbubbles of the carrier material 20.

Although FIG. 3 separately illustrates the imaging system 16 and the vibration generator 18, a single ultrasonic system could be used for both functions, with a relatively low power of ultrasonic energy being used to image the microbubbles 20 and a relatively high power of ultrasonic energy to collapse the microbubbles 20 to induce release of the drug 22.

Second Embodiment

The previous embodiment illustrates binding a carrier material, like an ultrasonic contrast agent, such as a gas microbubble, to a drug to form an ultrasonic contrast agent-drug complex that can be administered to an individual. The complex is administered to an individual in a manner such that the complex is trapped by mechanical or biological mechanisms at a specific site in the individual, then ultrasound or another imaging technique is used to detect the complex at a site of entrapment. The drug can be released at the site of entrapment by disrupting the complex, e.g., disintegrating the microbubble, by increasing the power, or altering the frequency, of the ultrasound energy.

The embodiment disclosed above utilizes mechanical mechanisms to trap the complex at a specific target site. In particular, an intravascular catheter system forced the complex into a vessel wall, thus trapping the complex and permitting diagnostic imaging and therapeutic release of the drug at a predetermined target site. A simpler version of the first embodiment could utilize an intravascular catheter to deliver the drug containing particles of a size greater than capillaries to the target area and allow mechanical trapping of the particles in the capillaries. However, it has been found that other mechanisms, and particularly biochemical mechanisms, also can be used to trap the ultrasonic contrast agent-drug complex at a predetermined target site. Biochemical trapping mechanisms permit administration of the complex at a site different from the target site. The complex then can travel, and is trapped, and collected, at the predetermined target site.

The second embodiment of the invention provides a therapeutic delivery system for site-specific delivery of a therapeutic drug. The delivery system preferably utilizes an ultrasonic contrast agent comprising gas microbubbles. The microbubbles have a drug and optionally, a targeting agent associated with the microbubble to provide site-specific delivery. The drug can be embedded in the microbubble shell, encapsulated in the microbubbles, or bound to the surface of the microbubbles. The targeting agent is bound to the surface of the microbubble shell and can be, for example, a monoclonal antibody bound to the outer surface of the microbubble, a chemical or electrochemical linkage, or a compound that is known to bind to specific sites in an individual, e.g., albumin microcapsules are known to bind to the reticuloendothelial system. The complexes, therefore, use biological properties to trap the microbubbles, and, therefore, the drug, at a specific target site in an individual.

An ultrasonic contrast agent-drug complex having a targeting agent for site-specific delivery (for example, a monoclonal antibody to a glycogen IIa/IIB receptor and a drug, like streptokinase, bound to a microbubble shell) is injected into the body. The microbubbles travel through the body, and because the microbubble shells of the ultrasonic contrast agent contain a targeting agent, like a specific monoclonal antibody, the microbubbles collect at a site where antibodies to the targeting agent are present.

Using low energy ultrasound imaging, movement of the complex, and positioning of the complex at the predetermined target site, is monitored. Then the drug is released at the target site by using high energy ultrasound energy, or other techniques known in the art (e.g., electromagnetic or mechanical vibrations), to disrupt or disintegrate the microbubbles. Specifically, the present invention provides a site-specific therapeutic delivery system comprising a carrier material, like an ultrasonic contrast agent (e.g., a microsphere containing a gas), a drug located in or on the shell of the microsphere, and a targeting agent, like an antibody for a specific site, bound to the shell.

Figure 4:
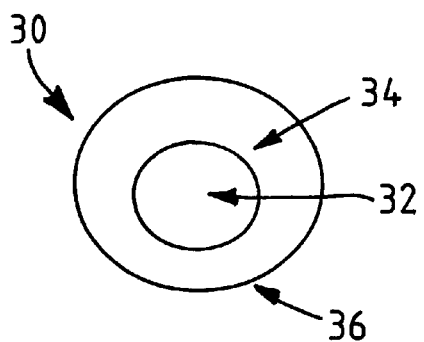
FIG. 4 schematically illustrates a second embodiment of a local drug delivery system in accordance with the invention.

An ultrasonic contrast agent-drug complex in accordance with the second embodiment of the invention is illustrated in FIG. 4. A complex 30 is a sphere having a core 32 comprising a gas. A shell 34 surrounds core 32 and has a surface 36. A drug can be incorporated into core 32, into shell 34, or bound to surface 36. A targeting agent is bound to surface 36 such that complex 30 can bind to a specific receptor site in the body and remain stationary for detection and for release of the drug. In practice, a plurality of targeting agents can be bound to surface 36 of complex 30. Complex 30 can be a micro-particle, a microbubble, a microsphere, or a micro-capsule.

Biochemical trapping of an ultrasonic contrast agent-drug complex is accomplished by incorporating a targeting agent into the complex. The targeting is selected such that the complex binds to a specific tissue or target site in the individual. The targeting agent can be, for example, a protein having an affinity to bind at the predetermined target site. The complex containing the drug, ultrasonic contrast agent, and targeting agent can be injected intravascularly, and the complex travels to and binds to, i.e., is trapped at, the predetermined target site by biochemical mechanisms.

After the complex has been trapped at the predetermined target site, the site may be ultrasonically imaged to confirm presence of the complex at the site. After imaging, or other diagnostic procedures, additional high gain or resonant frequency ultrasound energy is applied to the target site to induce microbubble rupture, and thereby release the drug (e.g., a thrombolytic drug carried to a site of vascular disruption).

Trapping of the complex by biochemical mechanisms is similar to the trapping of platelets along the endothelial surface within a blood vessel during periods of endothelial disruption (i.e., during periods of ischemia), wherein the initial attraction and trapping of the platelets in the endothelial lining is mediated by attraction of the glycoprotein Ib/IX complex along with the Von Willebrand's factor.

This is followed by spreading of platelets on the subendothelial matrix. Activation of platelets by collagen or other mediators, such as thrombin, leads to conformational changes in the integrin glycoprotein IIb/IIIa, and results in a second wave of platelet aggregation at the site of the subendothelial vascular wall disruption. This particular activation sequence is particularly well understood for thrombosis and ischemia.

Accordingly, the ultrasonic contrast agent-drug complex can be used to treat thrombosis or the effects of ischemia, and comprises: (a) a microbubble comprising a gas and shell, for example a protein shell, like an albumin shell, having (b) a targeting agent bound to the shell, for example an antibody, either glycoprotein Ib/IX with an autoantibody to Von Willebrand's factor, or, alternatively, to glycoprotein IIb/IIIc, and (c) a drug either bound to the shell or within the shell, for example a thrombolytic agent, like streptokinase or t-pa. Such a complex can be injected intravascularly, and the complex is biochemically trapped at a predetermined target site, for example, at a disrupted subendothelial ischemic vessel, at a thrombosis, or at a plaque rupture, where activated platelets are trapped and are aggregating.

The presence and accumulation of the complex at the predetermined target site can be monitored by ultrasound imaging techniques, and the drug, e.g., a thrombolytic drug, like streptokinase or t-pa, can be released by increasing the power, or altering the frequency, of the ultrasound energy.

In addition to treating vascular disruptions, the ultrasonic contrast agent-drug complexes of the present invention can be used to deliver other types of therapeutic agents, for example drugs used in oncology and against infectious diseases. In oncologic applications, the targeting agent can be an antitumor antibody (e.g., hepatic cellular antibody) which is bound to the shell of the microbubble and the drug can be a chemotherapy agent (e.g., 5FU) bound to or within the microbubble shell. The complex is injected intravascularly, and can be detected by ultrasound imaging. Then, after identifying that the complex has accumulated at the target site, the ultrasound energy or frequency is increased, thus releasing the chemotherapy agent at the specific and predetermined target site.

In infectious disease applications, antibodies to white blood cells can be bound to the microbubble shell, and the complex can be introduced into the infected zone. Following the detection of an increased signal which indicates positioning of the complex at the target site, the drug is released at the site of infection by increasing the ultrasound energy or frequency to disrupt or disintegrate the microbubbles.

It should be understood that the drug used in the ultrasonic contrast agent-drug complex is not limited to a specific type of drug, like thrombolytic drugs, but can be any drug capable of binding to, or being encapsulated in, the microbubble shell. For example, if the microbubble shell comprises albumin, the following, nonlimiting list of drugs are known to have the capability of binding to albumin, and can be used as the drug of the ultrasonic contrast agent-drug complex: acebutolol, acetylsalicylic acid, alfentanil, alprazolam, azlocillin, betamethasone, bleomycin, captopril, carbenicillin, cefamandole, cefazolin, cefonicid, ceforanide, cefotaxime, cefoxitin, clonidine, cloxacillin, cyclophosphamide, cytarabine, dexamethasone, dicloxacillin, diazepam, diazoxide, digitoxin, digoxin, diltiazem, diphenhydramine, disopyramide, doxorubicin, doxycycline, ceftazidime, ceftizoxime, cefuroxime, cephalexin, cephalothin, cephapirin, chloramphenicol, chloroquine, chlorothiazide, chlorpropormide, chlorthalidone, cimetidine, clofibrate, ibuprofen, imipramine, indomethacin, isosorbide dinitrate, ketoprofen, labetalol, lidocaine, lorazepam, lorcainide, meperidine, mercaptopurine, methadone, methicillin, erythromycin, ethambutol, fentanyl, flucytosine, flunitrazepam, fluorouracil, flurazepam, furosemide, gold sodium thiomalate, haloperidol, heparin, hexobarbital, hydrochlorothiazide, nortriptyline, oxacillin, oxazepam, phenobarbital, phenylbutazone, phenytoin, pindolol, prazosin, prednisolone, prednisone, protenecid, procainamide, propranolol, methothexate, methyldopa, methylprednisolone, metoprolol, metronidazole, mexiletine, mezlocillin, minocycline, morphine, moxalactam, nadolol, nafcillin, naproxen, nifedipine, nitrazepam, theopental, ticarcillin, timolol, tocainide, tolbutamide, tolmetin, triamterene, triazolam, trimethoprim, tubocurarine, valproic acid, verapamil, warfarin, protriptyline, pyrimethamine, quinidine, ranitidine, rifampin, salicylic acid, streptomycin, streptokinase, sulfadiazine, sulfamethoxazole, sulfisoxazole, ternazepam, terbutaline, tetracycline, theophylline, and tissue plasminogen activator (tpa).

Persons skilled in the art are aware of other drugs that are capable of binding to albumin, and similarly are aware, or can readily determine, drugs that are capable of binding to other materials comprising the microbubble shell. Similarly, persons skilled in the art are capable of selecting the proper targeting agent such that the complex is trapped at the predetermined target site.

With further respect to a complex useful for treating a vascular disruption, the complex can be prepared by initially treating the surface of an albumin microbubble with an autoantibody to glycoprotein IIb/IIa, then treating the surface with streptokinase. The resulting complex is injected intravascularly and trapped at sites of endothelial cell disruption. After injection, ultrasound images are obtained using a sufficiently low ultrasound energy to avoid destroying the trapped bubbles. After identifying the site specific placement of the complex, a high, continuously applied acoustic energy is used to destroy the microbubbles at the target site, and release the thrombolytic agent at the site of vascular cellular disruption.

Other methods also can be used to trap the ultrasonic contrast agent-drug complex in addition to using a protein. Nonlimiting examples include molecular adhesion and pharmacologic types of binding. For example, the surface glycoprotein from a plaque may be thin, as opposed to totally disrupted, and the microbubbles can be trapped.

It should be understood that introduction of the targeting agent and the drug onto the microbubble shell can be performed in sequence or simultaneously. In addition, introduction of the targeting agent and drug onto the microbubble shell can be performed after microbubble fabrication, before fabrication, or a combination thereof in order to provide a time release complex to position the targeting agent and drug on the outside, inside, or within the shell, or a combination thereof. The targeting agent and drug are bound to the microbubble shell by methods well known in the art.

In summary, the second embodiment of the invention is directed to methods for the controlled delivery of therapeutic compounds to specific target sites in an individual. The method comprises:

1. administering an ultrasonic contrast agent-drug complex to an individual, wherein the complex comprises an ultrasonic contrast agent, a drug, and a targeting agent.
2. monitoring the individual using ultrasound to determine an arrival and presence of the complex at a predetermined target site in the individual;
3. rupturing the complex at the target site using high power ultrasound or other energy forms to release the drug at the target site; and
4. imaging the target site using ultrasound techniques before, during, and after the release of the drug to monitor release of the drug.

The method steps, therefore, include:

1. preparing an ultrasonic contrast agent-drug complex;
2. introduction of the complex into an individual;
3. imaging a specific target site by low energy ultrasound imaging (e.g., Doppler or harmonics) to monitor arrival and positioning of the complex at the target site;
4. then applying sufficient energy to the target site to destroy the complex for delivery of the drug at the target site;
5. then performing low energy ultrasound imaging to determine whether release of the drug has occurred (i.e., no contrast effect should be observed if the complex has been disintegrated); and
6. modifying drug delivery and dosages by repeating the process.

Predetermined targeted sites include, for example, but are not limited to:

1. a glycogen IIA/IIB receptor, which is located in all vessel walls, and which can be blocked by a glycogen IIA/IIB receptor blocker and be detected by a monoclonal antibody to the receptor. Generally, this method of detecting specific receptor sites is performed using monoclonal antibodies;
2. specific electric or chemoelectrical methods that use positive or negative bindings;
3. use of known biological characteristics to predict that the microbubbles will be trapped after administration into an individual, e.g., the liver for albumin microspheres; and
4. fibrin and antithrombin can be targeted using antifibrin. In particular, if the antifibrin is bound to an albumin shell of a microbubble containing gas, the complex can be targeted to sites of atherosclerosis (atherosclerotic plaques).

The method of the second embodiment has several advantages, including simple administration and facile release of drugs, and the advantage of delivering potentially toxic drugs by systematic administrations at a low dose to the specific site where the drug is needed.

EXAMPLE 4

To a solution (10 cc) containing 500 mg of human serum albumin is added 50 mg of tissue plasminogen activator. The mixture is sonicated for 30 seconds using a Heat Systems 450 watt sonicator. The microbubbles thus formed are allowed to float to the top of the vial. The majority of the albumin solution is drawn off with a syringe and is replaced with an equal volume of albumin solution (5%). The tissue plasminogen activator loaded microspheres are infused into the left atrium of a pig heart at a flow rate of 1 cc/min. The region is continuously imaged as described in example 1. The bubbles are destroyed by acoustic pressure greater than 0.05 Mpa. The amount of reflected ultrasound as observed by the video intensity of the region decreases with continued insonation indicating that the albumin microspheres are destroyed thus releasing the tissue plasminogen activator.

Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A system for delivering a drug to a specific site and for monitoring the drug at the specific site, said system comprising:
   a carrier material which reflects or absorbs or emits electromagnetic or mechanical vibrations enabling the monitoring of said carrier material, said carrier material comprising an ultrasonic contrast agent composed of microbubbles having a diameter of between 1–1000 µm;
   a drug carried by said carrier material;
   a local-delivery catheter having said carrier material disposed therein and said drug carried by said carrier material disposed therein, said local-delivery catheter being designed such that said carrier material and said drug may be delivered to said specific site, said local-delivery catheter being designed so as to force said carrier material and said drug into an internal blood vessel wall at said specific site so that said carrier material and said drug are trapped therein;
   an ultrasonic imaging system that detects said carrier material at said specific site to confirm the presence of said carrier material at said specific site; and
   vibration generator associated with said imaging system, said vibration generator generating electromagnetic or mechanical vibrations that induce release of said drug from said carrier material when said carrier material is at said specific site by causing said microbubbles to collapse.

2. A system as defined in claim 1 wherein said carrier material comprises an ultrasonic contrast agent composed of microbubbles having a diameter of between 1–100 µm.

3. A system as defined in claim 1 wherein said local-delivery catheter comprises a balloon catheter.

4. A system for delivering a drug to a specific site and for monitoring the drug at the specific site, said system comprising:
   a carrier material which reflects or absorbs or emits electromagnetic or mechanical vibrations enabling the monitoring of said carrier material, said carrier material comprising microparticles, microbubbles, microspheres or microcapsules;
   a drug carried by said carrier material;
   a local-delivery catheter having said carrier material disposed therein and said drug carried by said carrier material disposed therein, said local-delivery catheter being designed such that said carrier material and said drug may be delivered to said specific site, said localdelivery catheter being designed so as to force said carrier material and said drug into an internal blood vessel wall at said specific site so that said carrier material and said drug are trapped therein;
   an imaging system that detects said carrier material at said specific site to confirm the presence of said carrier material at said specific site; and
   an apparatus associated with said imaging system, said apparatus generating electromagnetic or mechanical vibrations that induce release of said drug from said carrier material when said carrier material is at said specific site.

5. A system as defamed in claim 4 wherein said carrier material comprises an ultrasonic contrast agent composed of microbubbles.

6. A system as defined in claim 4 wherein said local-delivery catheter comprises a balloon catheter.

7. A system as defined in claim 4 wherein said imaging system comprises an ultrasonic imaging system.

8. A method of delivering a carrier material and a drug to a specific site using a local-delivery catheter and monitoring the carrier material and drug at the specific site, said method comprising the steps of:
   (a) disposing a carrier material which reflects or absorbs or emits electromagnetic or mechanical vibrations enabling the monitoring of said carrier material and a drug carried by said carrier material within a local-delivery catheter that is capable of delivering said carrier material and said drug to a specific site within a blood vessel, said carrier material comprising an ultrasonic contrast agent composed of microbubbles having a diameter of between 1–1000 µm;
   (b) after said carrier material and said drug are disposed within said local delivery catheter in said step (a), inserting said local-delivery catheter in said blood vessel;
   (c) when said local-delivery catheter is disposed within said blood vessel, using said local-delivery catheter to force said carrier material and said drug into an internal wall of said blood vessel at said specific site so that said carrier material and said drug are trapped at said specific site;
   (d) while said carrier material and said drug are trapped at said specific site in said blood vessel, using an imaging system to generate an image of said carrier material at said specific site in said blood vessel to confirm the presence of said carrier material at said specific site in said blood vessel; and
   (e) after the presence of said carrier material at said specific site in said blood vessel is confirmed at said step (d), generating electromagnetic or mechanical vibrations that induce release of said drug from said carrier material when said carrier material is at said specific site in said blood vessel by causing said microbubbles to collapse.

9. A method as defined in claim 8 wherein said step (a) comprises the step of disposing an ultrasonic contrast agent composed of microbubbles having a diameter of between 1–100 µm within said local delivery catheter.

10. A method as defined in claim 8 wherein said step (a) comprises the step of disposing said carrier material and said drug in a balloon catheter.

11. A method as defined in claim 8 wherein said step (d) comprises the step of detecting the presence of said carrier material at said specific site with an ultrasonic imaging system.

12. A method of delivering a carrier material and a drug to a specific site using a local-delivery catheter and monitoring the carrier material and drug at the specific site, said method comprising the steps of:
   (a) disposing a carrier material which reflects or absorbs or emits electromagnetic or mechanical vibrations enabling the monitoring of said carrier material and a drug carried by said carrier material within a local-delivery catheter that is capable of delivering said carrier material and said drug to a specific site within a blood vessel, said carrier material comprising microparticles, microbubbles, microspheres or microcapsules;
   (b) after said carrier material and said drug are disposed within said local delivery catheter in said step (a), inserting said local-delivery catheter in said blood vessel;

(c) when said local-delivery catheter is disposed within said blood vessel, using said local-delivery catheter to force said carrier material and said drug into an internal wall of said blood vessel at said specific site so that said carrier material and said drug are trapped at said specific site;

(d) while said carrier material and said drug are trapped at said specific site in said blood vessel, using an imaging system to generate an image of said carrier material at said specific site in said blood vessel to confirm the presence of said carrier material at said specific site in said blood vessel; and (e) after the presence of said carrier material at said specific site in said blood vessel is confirmed at said step (d), generating electromagnetic or mechanical vibrations that induce release of said drug from said carrier material when said carrier material is at said specific site in said blood vessel.

13. A method as defamed in claim 12 wherein said step (a) comprises the step of disposing an ultrasonic contrast agent composed of microbubbles.

14. A method as defamed in claim 12 wherein said step (a) comprises the step of disposing said carrier material and said drug in a balloon catheter.

15. A method as defamed in claim 12 wherein said step (d) comprises the step of detecting the presence of said carrier material at said specific site with an ultrasonic imaging system.

* * * * *